(12) United States Patent
Johnson

(10) Patent No.: US 9,782,273 B2
(45) Date of Patent: Oct. 10, 2017

(54) FLEXIBLE COUPLING SYSTEM

(71) Applicant: Alwyn P. Johnson, Englewood, CO (US)

(72) Inventor: Alwyn P. Johnson, Englewood, CO (US)

( * ) Notice: Subject to any disclaimer, the term of this patent is extended or adjusted under 35 U.S.C. 154(b) by 0 days.

(21) Appl. No.: 15/079,025

(22) Filed: Mar. 23, 2016

(65) Prior Publication Data

US 2016/0281405 A1 Sep. 29, 2016

Related U.S. Application Data

(60) Provisional application No. 62/136,977, filed on Mar. 23, 2015.

(51) Int. Cl.
*A61F 2/50* (2006.01)
*A61F 5/01* (2006.01)

(52) U.S. Cl.
CPC .............. *A61F 2/50* (2013.01); *A61F 5/01* (2013.01); *A61F 2002/5007* (2013.01); *Y10T 16/540345* (2015.01)

(58) Field of Classification Search
CPC ..... E05D 11/082; E05D 3/02; E05D 11/0054; E05D 2011/0072; Y10T 16/533; Y10T 16/5387; Y10T 16/540255; Y10T 16/54035; Y10T 16/54038; Y10T 16/540345; A61F 2/50; A61F 5/01; A61F 2002/5007
USPC ..... 16/303, 330, 340, 341, 342, 250; 602/16
See application file for complete search history.

(56) References Cited

U.S. PATENT DOCUMENTS

| | | | |
|---|---|---|---|
| 2,712,742 A | 7/1955 | Neidhart | |
| 2,729,442 A | 1/1956 | Neidhart | |
| 2,861,796 A | 11/1958 | Rohr | |
| 2,950,103 A | 8/1960 | Ruf | |
| 2,994,213 A | 8/1961 | Arnold et al. | |
| 3,012,767 A | 12/1961 | Jones, Sr. | |
| 3,601,424 A | 8/1971 | Badland et al. | |
| 5,788,265 A | 8/1998 | McLaughlin | |
| 6,588,778 B1 | 7/2003 | McLaughlin | |
| 6,925,684 B2 * | 8/2005 | Kang | G06F 1/1616 16/264 |
| 7,117,563 B2 * | 10/2006 | Chen | G06F 1/1616 16/303 |
| 7,213,301 B2 * | 5/2007 | Sakai | H04M 1/0216 16/303 |
| 7,565,718 B2 * | 7/2009 | Duan | H04M 1/0216 16/303 |
| 7,634,838 B2 * | 12/2009 | Ge | H04M 1/0216 16/303 |

(Continued)

*Primary Examiner* — William Miller
(74) *Attorney, Agent, or Firm* — Oppedahl Patent Law Firm LLC

(57) ABSTRACT

An apparatus for joining two members, comprising a central assembly within a first housing, the central assembly comprising a rotor or rotational member, a pin attached at one end to the rotor or rotational member, a base circumferentially disposed about the pin and attached thereto, a resistance member in connection with the pin, at least one compression member in connection with the resistance member, at least one intermediary member disposed between the at least one compression member and the base, a second housing in connection with the pin and first and second arm mechanisms attached at opposing distal ends of the pin.

1 Claim, 7 Drawing Sheets

(56) References Cited

U.S. PATENT DOCUMENTS

| | | | | |
|---|---|---|---|---|
| 7,725,989 B2* | 6/2010 | Huang | ................... | G06F 1/162 16/302 |
| 7,735,198 B2* | 6/2010 | Petermann | ............. | F16M 11/06 16/340 |
| 7,810,648 B2 | 10/2010 | Takev et al. | | |
| 8,006,346 B2* | 8/2011 | Zhang | ................ | H04M 1/0216 16/303 |
| 8,056,186 B2* | 11/2011 | Zhang | ................ | H04M 1/0216 16/303 |
| 8,336,167 B2* | 12/2012 | Kim | ................... | H04M 1/0216 16/303 |
| 8,683,654 B2* | 4/2014 | Chen | ..................... | E05D 11/087 16/298 |
| 2004/0000769 A1 | 1/2004 | Few | | |
| 2008/0155784 A1* | 7/2008 | Hsu | ..................... | H04M 1/0216 16/303 |
| 2009/0300882 A1* | 12/2009 | Hayashi | .................... | F16F 1/12 16/303 |
| 2010/0000046 A1* | 1/2010 | Park | ..................... | E05D 7/1011 16/250 |
| 2010/0050385 A1* | 3/2010 | Zhang | ................ | H04M 1/0216 16/303 |
| 2010/0180401 A1* | 7/2010 | Duan | ..................... | G06F 1/1616 16/250 |
| 2011/0203077 A1* | 8/2011 | Kitamura | ............ | H04M 1/0216 16/297 |
| 2012/0084943 A1* | 4/2012 | Ahn | ..................... | G06F 1/1681 16/250 |
| 2014/0075720 A1* | 3/2014 | Caffin | .................. | E05F 1/1215 16/298 |
| 2015/0121654 A1* | 5/2015 | Novin | ...................... | E05D 3/02 16/273 |

* cited by examiner

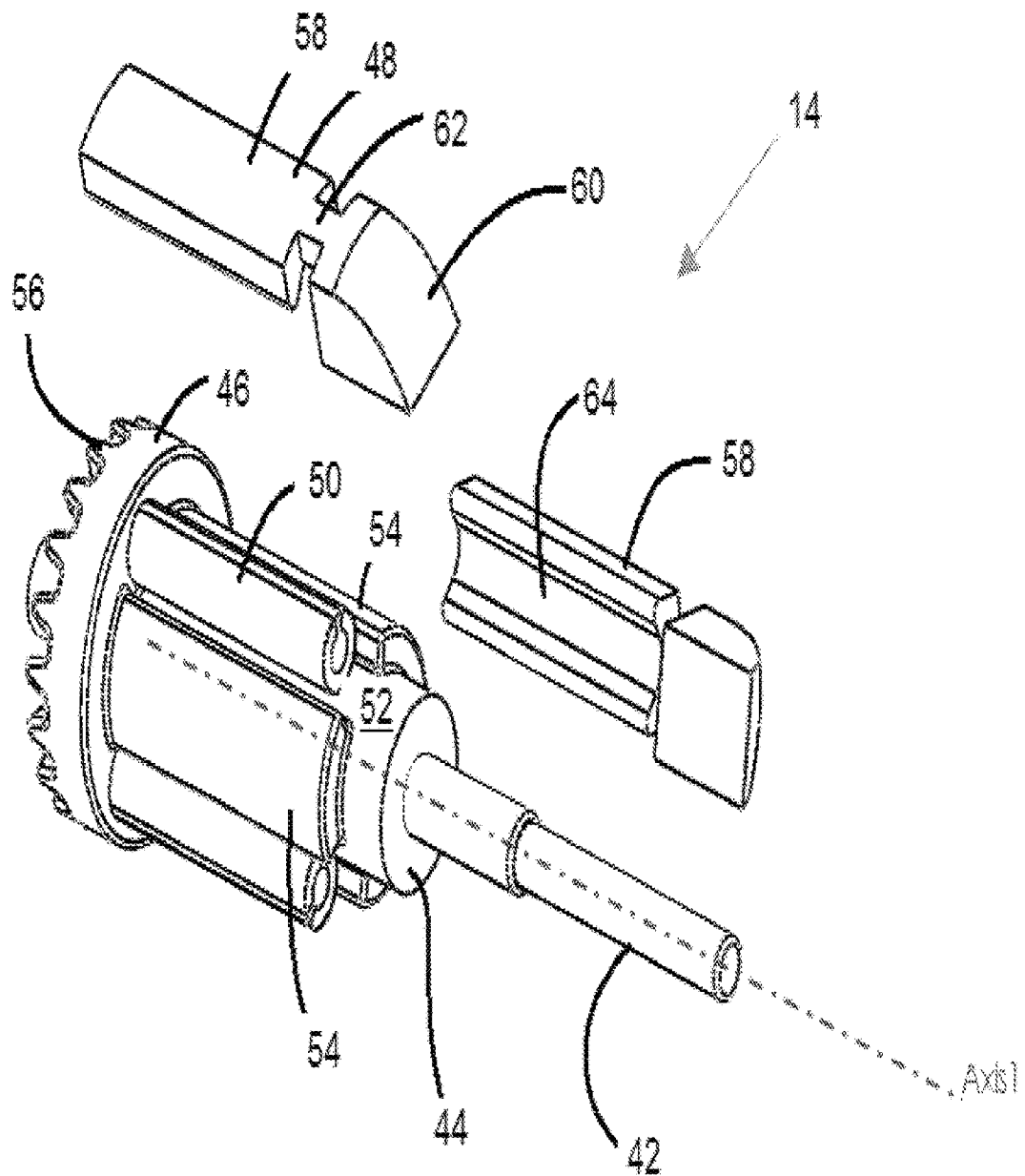
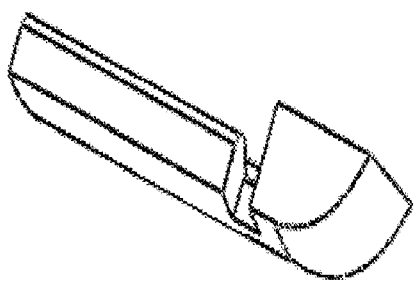
Fig. 4

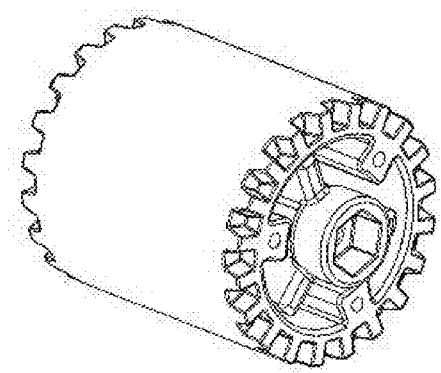
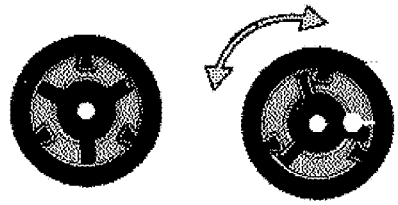
Fig. 8A  Fig. 8B  Fig. 8C
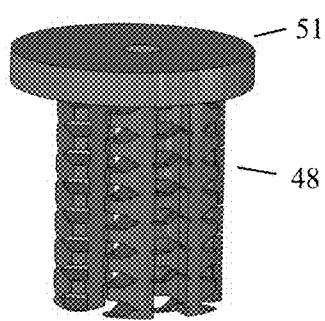
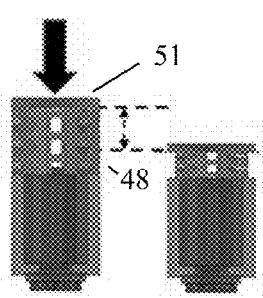
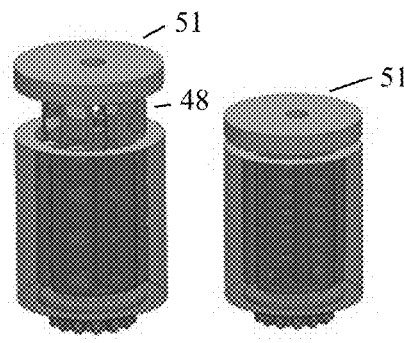
Fig. 9A  Fig. 9B  Fig. 9C  Fig. 9D  Fig. 9E
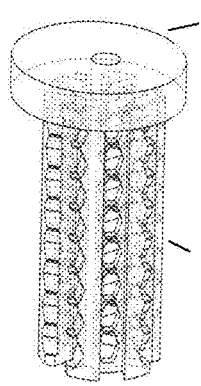
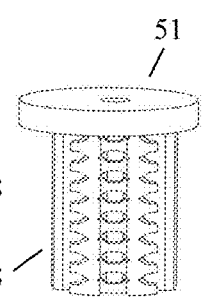
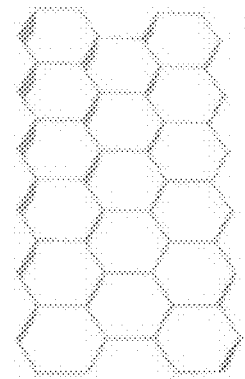
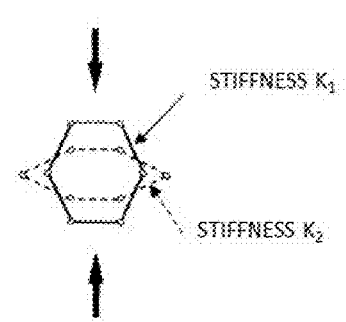
Fig. 10A  Fig. 10B  Fig. 10C  Fig. 10D

FLEXIBLE COUPLING SYSTEM

BACKGROUND OF THE INVENTION

A joint between two structural members requires a connecting point and a manner of connecting the two members. Depending upon the type of joint and its requirements for operation, the joint may be either fixed or movable. In the case of a movable joint, the connection should be flexible. This flexibility allows the joint to operate within a defined range-of-motion. When unrestricted range-of-motion of a joint is not desired, the manner of connection must provide at least some resistance to the members.

The development of modern prostheses and artificial limbs provides a specific example of these requirements in practice. Any artificial limb containing a joint must travel within a natural range-of-motion in order to approximate human anatomy and thus allow the most utility possible. While utility may be of primary concern, the limitations of the rest of the human body cannot be ignored. For this reason, any artificial joint must also provide resistance to unrestricted motion.

BRIEF SUMMARY OF THE INVENTION

Disclosed herein is a system for coupling two separate structural members while providing a measure of both flexibility of the connection and resistance to the full range-of-motion.

BRIEF DESCRIPTION OF THE DRAWINGS

Referring now to the attached drawings which form a part of this original disclosure:

FIG. 4 is an exploded view of a central assembly of the flexible coupling system of FIG. 1 according to an embodiment of the invention;

FIG. 8A is a perspective view of a central assembly of the flexible coupling system of FIG. 2 according to an embodiment of the invention.

FIGS. 8B and 8C illustrate a lateral view of a central assembly of the flexible coupling system of FIG. 2 depicting at least one contact to restrict motion.

FIG. 9A is a perspective view of a resistance member of the flexible coupling system of FIG. 1 with attached compression members.

FIGS. 9B and 9C illustrate a front view of a central assembly in contact with a resistance member and attached compression members of the flexible coupling system of FIG. 1.

FIGS. 9D and 9E illustrate a perspective view of a central assembly in contact with a resistance member and attached compression members of the flexible coupling system of FIG. 1.

FIG. 10A is a detailed perspective view of a resistance member of the flexible coupling system of FIG. 2 with attached compression members according to an embodiment of the invention.

FIG. 10B depicts a resistance member of the flexible coupling system of FIG. 2 with attached compression members according to an embodiment of the invention.

FIG. 10C depicts a lattice structure of a compression member according to an embodiment of the invention.

FIG. 10D depicts the compression of an individual lattice cell within a compression member according to an embodiment of the invention.

DETAILED DESCRIPTION OF THE PREFERRED EMBODIMENTS

Selected embodiments of the present invention will now be explained with reference to the drawings. It will be apparent to those skilled in the art from this disclosure that the following descriptions of the embodiments of the present invention are provided for illustration only and not for the purpose of limiting the invention as defined by the appended claims and their equivalents.

Figure 1:
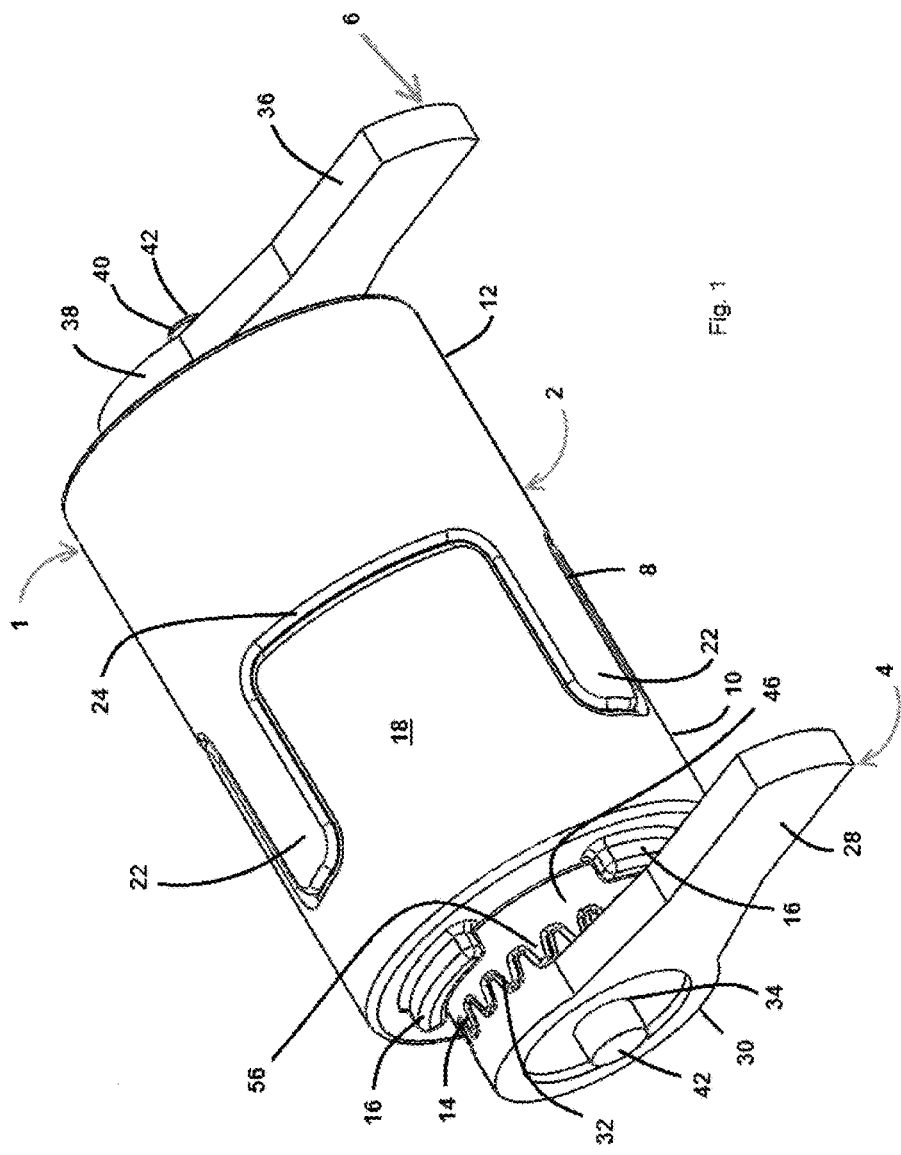
FIG. 1 is a perspective view of a flexible coupling system according to an embodiment of the present invention.
Figure 2:
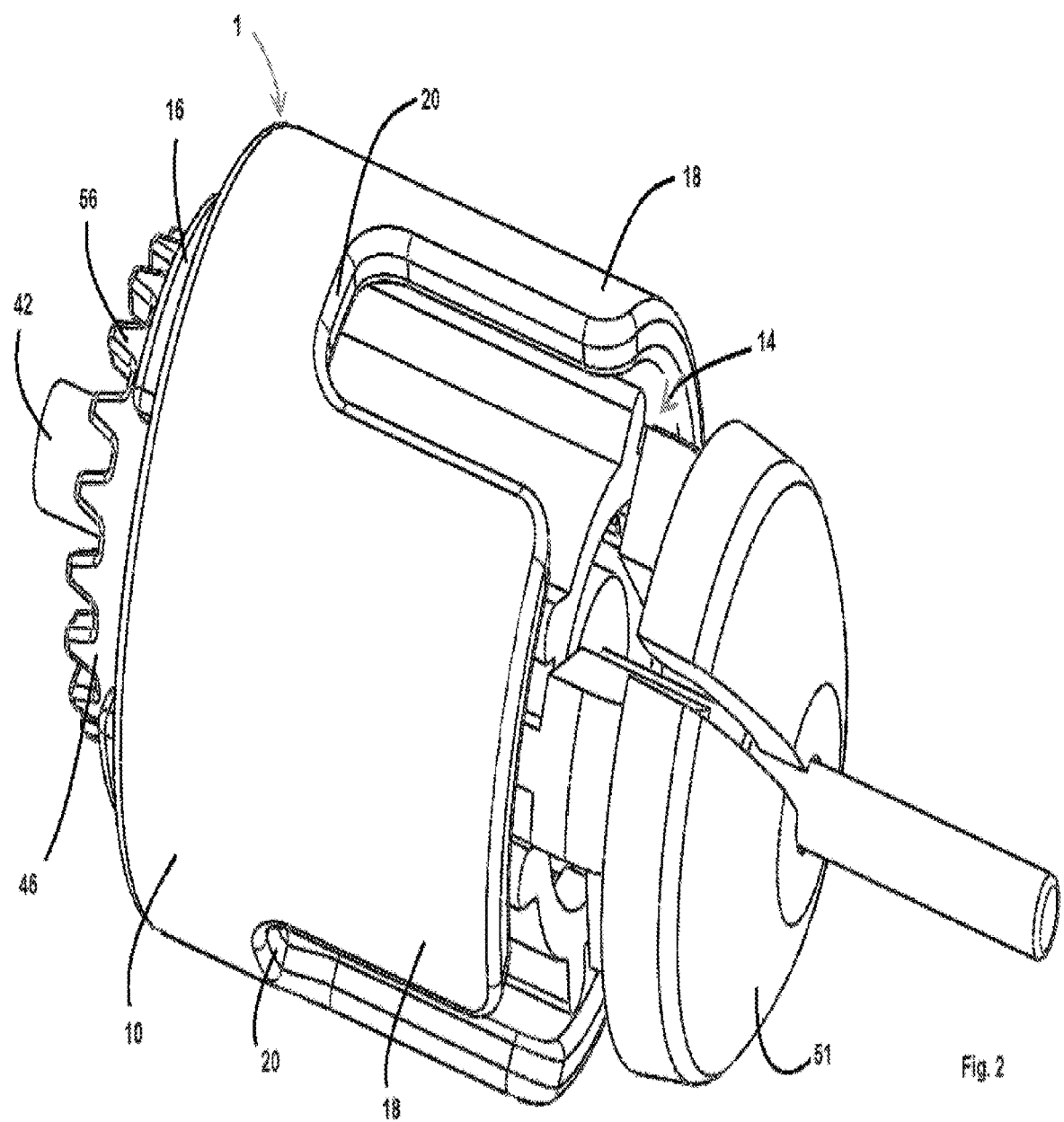
FIG. 2 is a perspective view of the flexible coupling system of FIG. 1 with the first and second arm mechanism and the second housing member removed for clarity according to an embodiment of the present invention.
Figure 3:
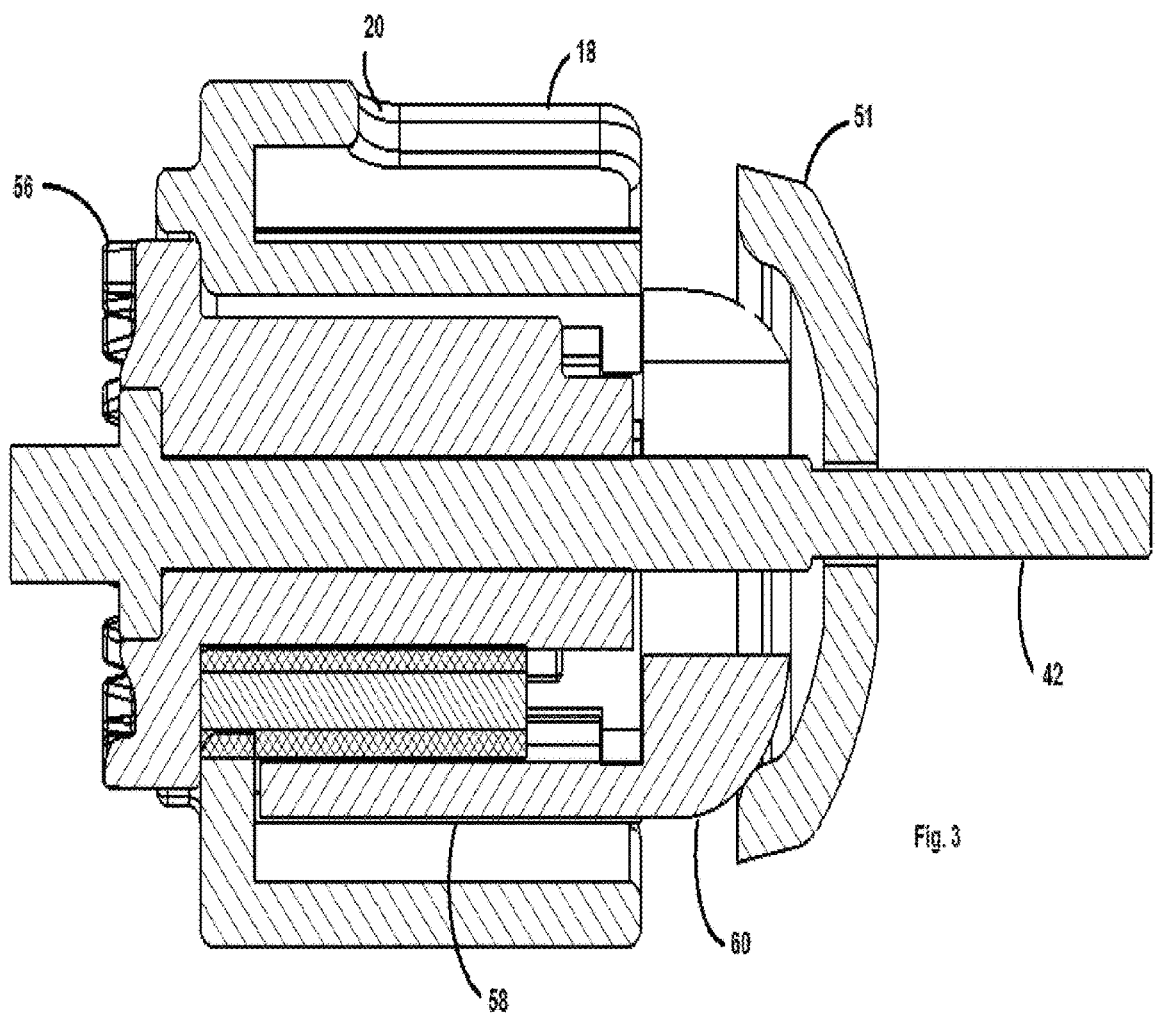
FIG. 3 is a cross-sectional view of the flexible coupling system of FIG. 2 according to an embodiment of the present invention.
Figure 5:
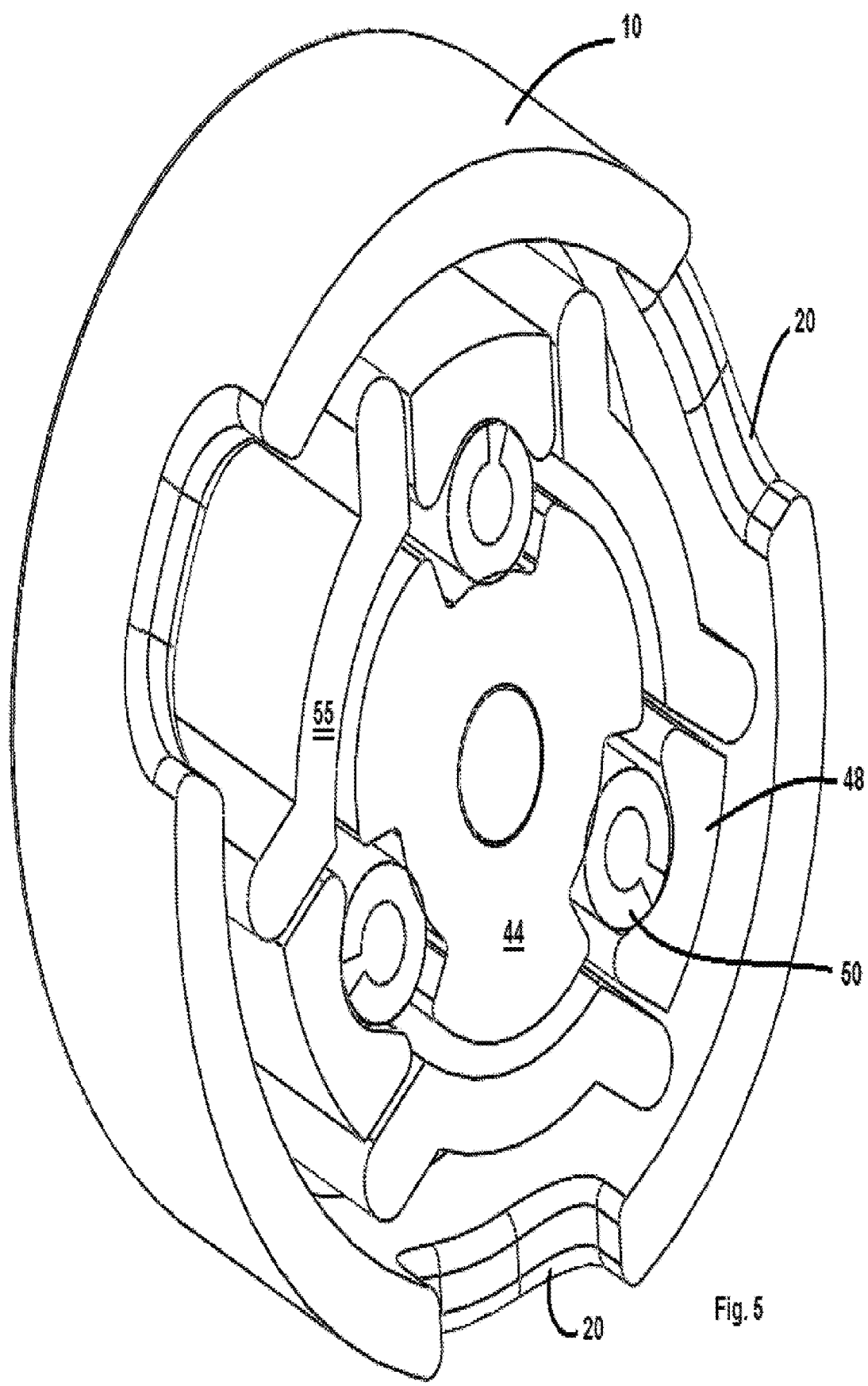
FIG. 5 is a cross-sectional view of the flexible coupling system of FIG. 2 according to an embodiment of the present invention.
Figure 6:
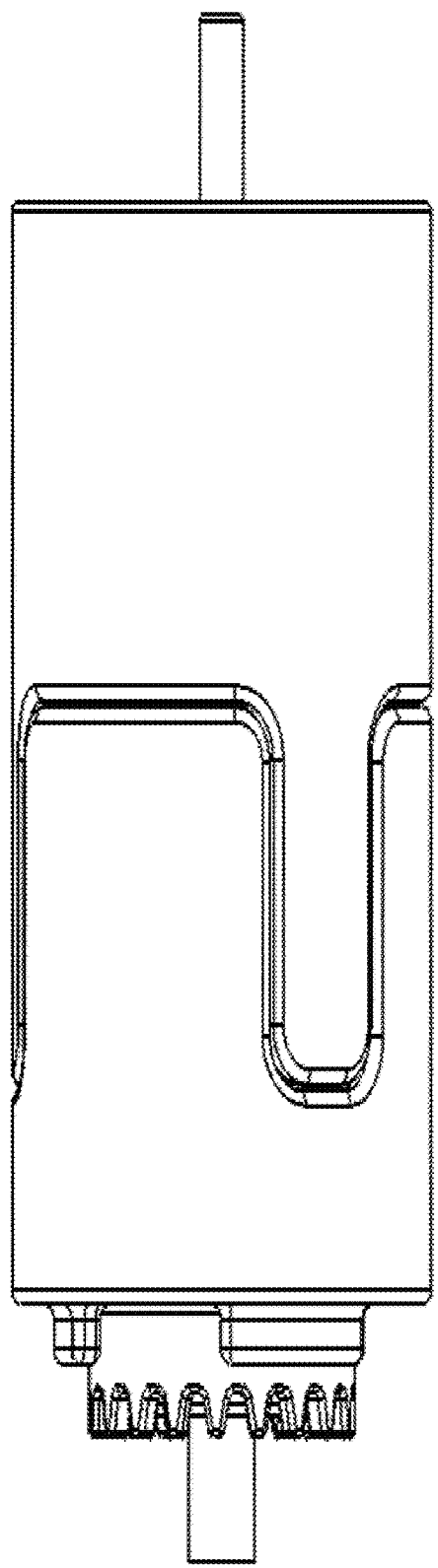
FIG. 6 is a plan view of the flexible coupling system of FIG. 1 with the first and second arm mechanisms removed for clarity according to an embodiment of the present invention.
Figure 7:
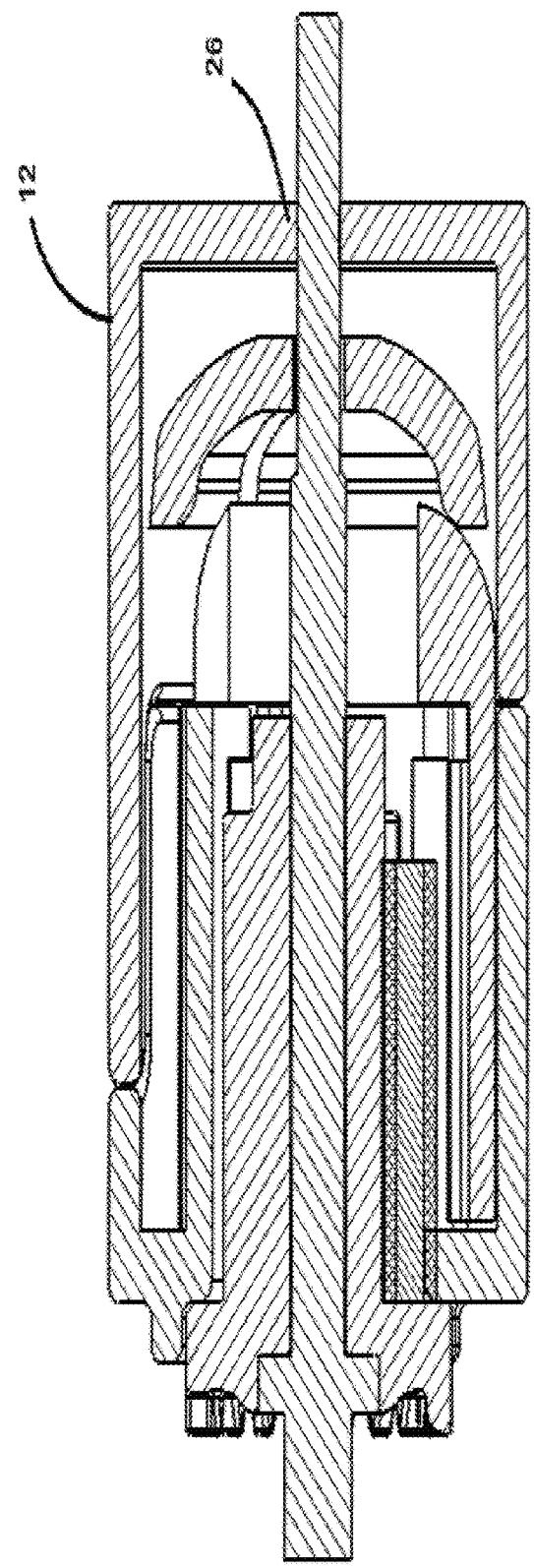
FIG. 7 is a cross-sectional view of the flexible coupling system of FIG. 6 according to an embodiment of the present invention.

Referring initially to FIG. 1, a flexible coupling system 1 is illustrated in accordance with a first embodiment of the present invention. The flexible coupling system 1 includes a coupling assembly 2, a first arm mechanism 4 and a second arm mechanism 6. The first arm mechanism 4 and the second arm mechanism 6 connect to the coupling assembly 2 at respective ends of the coupling assembly 2. The first arm mechanism 4 and the second arm mechanism 6 are for connection with that which requires dampening or selective flexibility. For example, the flexible coupling system 1 may be positioned at a joint of a structural system. The first arm mechanism 4 and the second arm mechanism 6 may connect the coupling assembly 2 to structural members (not shown) at the joint. For example, the flexible coupling assembly 1 may be used as one or more of the adjustable tensioners disclosed in the orthosis of U.S. patent application Ser. No. 13/899,541, incorporated by reference herein in its entirety. The flexible coupling assembly 1 may also be used as an artificial joint in prostheses, such as artificial arms and legs, for example.

Referring to FIGS. 1-7, the coupling assembly 2 includes a housing 8 having a first housing member 10, a second housing member 12 and a central assembly 14. The first housing member 10 and the second housing member 12 mate to encase the central assembly 14 within a cavity formed by the first housing member 10 and the second housing member 12.

The first housing member 10 includes one or more extensions 16 circumferentially disposed at a lateral side of the first housing member 10. The one or more extensions 16 extend longitudinally from the lateral side of the first housing member 10 and are curved to follow the contour of a side portion of the central assembly 14. The first housing member 10 further includes one or more finger portions 18 and one or more recessed portions 20.

The second housing member 12 includes one or more finger portions 22 and one or more recessed portions 24. The finger portions 18 of the first housing member 10 are slidably disposed in the recessed portions 24 of the second housing member 12. The finger portions 22 of the second housing member 12 are slidably disposed in the recessed portions 20 of the first housing member 10. Finger portions 18,22 have an arcuate cross-section to form, when engaged adjacent to one another, a cylindrical shell about the central assembly 14.

The second housing member 12 has an opening 26 for a side portion of the central assembly 14 to extend therethrough. The opening 26 is disposed on a side of the housing 8 opposite the extensions 16.

The first arm mechanism 4 includes an extended portion 28 and a circular portion 30. At one end, the extended portion 28 is integral with the circular portion 30 and extends from the circular portion 30. At another end, the extended portion 28 preferably engages the structural member (not shown) at a joint. The circular portion 30 has a plurality of circumferentially disposed teeth 32 extending inwardly towards the central assembly 14 and an inner aperture 34 sized and configured to receive a portion of the central assembly 14. The teeth 32 extend substantially parallel to the longitudinal axis of the central assembly 14.

The second arm mechanism 6 includes an extended portion 36 and a circular portion 38. At one end, the extended portion 36 is integral with the circular portion 38 and extends from the circular portion 38. At another end, the extended portion 36 preferably engages the structural member (not shown) at a joint. The circular portion 30 has an inner aperture 40 sized and configured to threadedly engage a portion of the central assembly 14.

The central assembly 14 includes a pin member 42, a base member 44, a rotor or rotational member 46, one or more compression members 48, one or more intermediary members 50 and a resistance member 51. The pin member 42 is a longitudinally extending rod-like member that extends through the base member 44, the rotor or rotational member 46, the compression members 48, the intermediary members 50 and the resistance member 51. The pin member 42 may rotate in a clockwise or counterclockwise direction about its longitudinal axis A. The pin member 42 engages the circular portion 30 of the first arm mechanism 4 at the aperture 34. The pin member 42 engages the circular portion 38 of the second arm mechanism 6 at the aperture 40.

The base member 44 is a substantially cylindrical member that is non-rotatably disposed on the pin member 42 between ends of the pin member 42. The base member 44 supports the intermediary members 50 by providing a support surface 52 for each of the intermediary members 50 to rest thereon and providing raised segments 54 between the intermediary members 50. The support surface 52 and the raised segments 54 essentially provide a stall in which the intermediary members 50 are disposed. One or more additional supports 55 may optionally be provided between the compression members 48 and the intermediary members 50. The additional supports 55 may be rigidly fixed and extend from the rotor or rotational member 46.

The rotor or rotational member 46 is fixedly and non-rotatably attached to the base member 44 and/or the pin member 42. A lateral surface of the rotor or rotational member 46 provides a backing for the stall in which the intermediary members 50 are disposed. The rotor or rotational member 46 includes a plurality of circumferentially disposed teeth 56. The teeth 56 extend outwardly towards the teeth 32 of the circular portion 30. The teeth 56 extend substantially parallel to the longitudinal axis A of the pin member 42 of the central assembly 14. The teeth 32,56 are sized and configured to selectively engage such that the first arm mechanism 4 and the rotor or rotational member 46 are non-rotatably engaged. That is, the teeth 32 can be disengaged from the teeth 56 then the first arm mechanism 4 is rotated relative to the rotor or rotational member 46 to a desired position. The teeth 32 can then be reengaged with the teeth 56 such that the first arm mechanism 4 is now at a new desired angle and non-rotatably engaged with the rotor or rotational member 46.

The compression members 48 are generally a rigid, elongate rectangular member for pressing the intermediary members 50 into the base member 44. The intermediary members 50 are generally an elastomeric, elongate member to be pressed against the base member 44. In some embodiments, the intermediary member 50 can have a circular cross-sectional shape or can have other cross-sectional shapes as desired for dampening/resisting rotation of the pin member 42. For example, the intermediary member 50 may have an elliptical, polygonal or non-uniform cross-sectional shape.

In the embodiment shown in FIG. 4, the flexible coupling system 1 includes four compression members 48 and four corresponding intermediary members 50. However, it will be apparent to one of skill in the art from this disclosure that the flexibly coupling system 1 may have more or less compression members 48 and corresponding intermediary members 50 to provide a desired range of rotation and/or resistance for the pin member 42.

The compression member 48 includes a first end section 58, a second end section 60 and a neck section 62 between the first end section 58 and the second end section 60. The first end section 58 has a groove portion 64 sized and configured to receive the intermediary member 50. The groove portion 64 is for receiving the intermediary member 50 and runs substantially parallel to the longitudinal axis A. In this embodiment, the groove portion 64 is concave and is configured to have a contour that substantially follows at least a portion of the periphery of the intermediary member 50 when in a compressed state.

The second end section 60 is connected to the first end section 58 by the neck section 62. It will be apparent to one of ordinary skill in the art from this disclosure that the neck portion 62 can be of various widths and can even be the same width as the first or second end section 58,60. The second end section 60 has an arcuate portion 66. The arcuate portion 66 contacts the resistance member 51. As the resistance member 51 rotates in one direction, the arcuate portion 66 is forced radially inward towards the pin member 42. As the resistance member 51 rotates in another direction, the arcuate portion 66 is allowed to move radially outwardly away from the pin member 42.

The radial movement of the arcuate portion 66 is accomplished by rotating the resistance member 51. The resistance member 51 has an inner lip (not shown), on which at least a portion of the arcuate portions 66 are received. The resistance member 51 is threadedly engaged to the pin member 42 and tightened or loosened as it is rotated.

The channels extend substantially parallel to the longitudinal axis A. Each of the channels 32 has opposing walls 38 that serve to contain the intermediary member 10 under compression. The walls 38 make up sides of the ridges 34. That is, each ridge 34 has two opposing walls 38 on its side. Each of the ridges 38 is disposed between two channels 32. The ridges are elongate and extend substantially parallel to the longitudinal axis A, as well as radially outward from the pin member 42. The channels 32 and the ridges 34 are sized and configured to receive at least a portion of the intermediary member 10. The annular groove 36 is disposed at the middle section 28 of the pin member 4. The annular groove 36 is sized and configured to receive at least a portion of the arcuate section 22 of the cam portion 20 therein.

In operation, the resistance member 51 applies a radially inward force onto the arcuate portion 66. The amount of desired radially inward force can be selected by rotating the resistance member 51. The radially inward force causes the compression members 48 and the intermediary members 50 to enter into varying degrees of a compressed state. The greater the compressed state, the more radially inward position of the compression members 48 and the more deformation of the intermediary members 50, thereby causing more resistance to rotation of the pin member 42. Thus, the resistance member 51 can be rotated in either direction to allow a desired amount of rotation of the pin member 42. The pin member 42 may rotate in a clockwise or counterclockwise direction about its longitudinal axis A until met with resistance in an amount equal to or greater than the rotation force applied to the pin member 42.

In a compressed state of the compression member 48, the compression member 48 deforms the intermediary members 50. In the compressed state, one portion of the intermediary member 50 conforms to the shape of the groove portion 64 while another portion conforms to the shape of the stall formed by the support surface 52 and the segments 54.

According to another embodiment of the invention, the compression members 48 are attached to the resistance member 51 and provide varying degrees of compressibility as determined by the initial depth of the resistance member 51 relative to the first housing member 10 of the flexible coupling assembly 2. In other embodiments, the combination of the teeth and compression components enable variation of the coupling stiffness based on a determined angle, which may be preset or modified during operation. In some embodiments, the compression members 48 may be formed in a lattice structure.

Disclosed herein is an apparatus for joining two members, comprising a central assembly within a first housing, the central assembly comprising a rotor or rotational member, a pin attached at one end to the rotor or rotational member, a base circumferentially disposed about the pin and attached thereto, a resistance member in connection with the pin, at least one compression member in connection with the resistance member, at least one intermediary member disposed between the at least one compression member and the base, a second housing in connection with the pin and first and second arm mechanisms attached at opposing distal ends of the pin.

GENERAL INTERPRETATION OF TERMS

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Also, the terms "part," "section," "portion," "member" or "segment" when used in the singular can have the dual meaning of a single part or a plurality of parts. Finally, terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

The invention claimed is:

1. An apparatus for joining two members, comprising:
    a central assembly within a first housing, the central assembly comprising:
        a rotational member;
        a pin attached at one end to the rotational member, said pin having an axis of rotation;
        a base circumferentially disposed about the pin and attached thereto;
        a resistance member in connection with the pin;
        at least one compression member in connection with the resistance member, the compression member positioned parallel to the pin and said axis of rotation;
        at least one intermediary member disposed between the at least one compression member and the pin and in contact with the base, the intermediary member positioned parallel to the pin and said axis of rotation;
    a second housing in connection with the pin; and
    first and second arm mechanisms attached at opposing distal ends of the pin and extending radially outward from the pin.

* * * * *